United States Patent [19]

Heather et al.

[11] 4,325,881

[45] Apr. 20, 1982

[54] DEBROMINATION

[75] Inventors: James B. Heather, Hercules, Calif.; David R. White, Kalamazoo, Mich.

[73] Assignee: The Upjohn Company, Kalamazoo, Mich.

[21] Appl. No.: 263,833

[22] Filed: May 15, 1981

Related U.S. Application Data

[63] Continuation-in-part of Ser. No. 213,447, Dec. 5, 1980.

[51] Int. Cl.$^3$ ............................................... C07J 7/00
[52] U.S. Cl. ............................................... 260/397.45
[58] Field of Search .................................... 260/397.45

[56] References Cited

U.S. PATENT DOCUMENTS 3,480,622  11/1969  Barton ........................... 260/239.55

OTHER PUBLICATIONS

Tetrahedron Letters 43, 3151 (1964).
J. Am. Chem. Soc. 88, 3016 (1966).
J. Am. Chem. Soc. 79, 1130 (1957).

*Primary Examiner*—Elbert L. Roberts
*Attorney, Agent, or Firm*—Bruce Stein

[57] ABSTRACT

A process for 9α-debromination of 9α-bromo-11β-hydroxy steroids without eliminating the 11β-hydroxyl group utilizing chromous chloride or chromous sulfate and thioglycolic acid.

8 Claims, No Drawings

DEBROMINATION

DESCRIPTION

CROSS REFERENCE TO RELATED APPLICATIONS

This patent application is a continuation-in-part of co-pending patent application Ser. No. 213,447, filed Dec. 5, 1980.

BACKGROUND OF THE INVENTION

U.S. Pat. No. 3,480,622 discloses a process for debromination of a 9α-bromo-11β-hydroxy steroid by reaction with a salt of a polyvalent metal (Cr) which is in a lower state of valence (+2) capable of being oxidized to a higher state (+3) in the presence of a substance (thiol) capable of providing hydrogen radicals. The reducing agent was preferably a chromous salt of an organic carboxylic acid, preferably chromous acetate. Listed as suitable to provide hydrogen radicals were a number of substances, including thiols which could carry various substituents including carboxyl groups. However, it was preferred that the substituent be lower alkyl or unsubstituted aryl groups such as phenyl. A mechanistic explanation for the above is set forth in Tetrahedron Letters 43, 3151 (1964) and a more detailed account is found in J. Am. Chem. Soc. 88, 3016 (1966).

J. Fried and E. F. Sabo in J. Am. Chem. Soc. 79, 1130 (1957) discussed the problems of trying to debrominate a 9α-bromo-11β-hydroxy steroid to form the corresponding 11β-hydroxy steroid. Using chromous chloride and zinc in acetic acid, they obtained the pure 9(11)-dehydro compound in about 80% yield, page 1131.

BRIEF DESCRIPTION OF THE INVENTION

Refer to Charts A thru D.

Disclosed is a process for the preparation of an 11β-hydroxy steroid which comprises reacting a 9α-bromo- or 9α-chloro-11β-hydroxy steroid with chromous sulfate or chromous chloride or mixtures thereof and HS—CH$_2$—COOH.

Further disclosed is a process for the preparation of an 11β-hydroxy pregnane (II), which comprises reacting a 9α-halo-11β-hydroxy pregnane (I) with chromous chloride or chromous sulfate or mixtures thereof and HS—CH$_2$—COOH.

Also disclosed is a process for the preparation of an 11β-hydroxy androstane (IV), which comprises reacting a 9α-halo-11β-hydroxy androstane (III) with chromous chloride or chromous sulfate or mixtures thereof and HS—CH$_2$—COOH.

Disclosed is a process for the preparation of an 11β,17α-dihydroxyprogesterone (VI), which comprises reacting a 9α-halo-11β,17α-dihydroxyprogesterone (V) with chromous chloride or chromous sulfate, or mixtures thereof, and HS—CH$_2$—COOH.

Also disclosed is a process for the preparation of an 11β-hydroxyprogesterone (VIII), which comprises reacting a 9α-halo-11β-hydroxyprogesterone (VII) with chromous chloride or chromous sulfate, or mixtures thereof, and HS—CH$_2$—COOH.

DETAILED DESCRIPTION OF THE INVENTION

A large number of commercially available pharmacologically active steroids have 11β-hydroxy-Δ$^4$-3-keto or 11β-hydroxy-Δ$^{1,4}$-3-keto functionality. These steroids include hydrocortisone, 11β-hydroxyprogesterone, prednisolone, 6α-methylprednisolone, and 16-methylprednisolone and analogues thereof. In the process of introducing the 11β-hydroxyl group, a 9α-halo (chlorine or bromine atom) is also sometimes introduced. Therefore, it would be desirable to have a process which would dehalogenate a 9α-chloro or 9α-bromo-11β-hydroxy steroid (I, III, V or VII) to the corresponding 11β-hydroxy steroid (II, IV, VI or VIII). Most known processes produce too much of the 9(11)-unsaturated by-product to be of value, see J. Am. Chem. Soc. 79, 1130 (1957). A process capable of being developed commercially was disclosed in U.S. Pat. No. 3,480,622.

The process of U.S. Pat. No. 3,480,622 involved reacting a 9α-bromo-11β-hydroxy steroid (I, III, V, or VII) with a salt of a polyvalent metal in which the metal is capable of being oxidized to a higher valence state in the presence of a substance capable of providing hydrogen free radicals.

In U.S. Pat. No. 3,480,622, the metal ion reducing agents included ferrous, titanous, thallous, stannous and chromous salts. Chromous salts were preferred used as the salt of an organic carboxylic acid, preferably a lower ($C_{1-6}$) alkanoic acid such as acetic, propionic or butyric. Chromous acetate was "especially suitable."

It has been discovered that chromous chloride or chromous sulfate or mixtures thereof are preferable reducing agents. Chromous chloride or chromous sulfate have the advantage of greater ease of preparation, storage and handling. These reagents can also be prepared in higher yield than chromous acetate. A slight excess of chromous sulfate over theory brings about rapid (5 to 15 minutes) and complete reduction of 9α-bromo-11β-hydroxysteroids when used with the co-reductant thioglycolic acid.

In U.S. Pat. No. 3,480,622, the substances capable of providing hydrogen radicals included $H_3PO_2$, hydrides such as triarylsilanes or triaryltin hydrides, 1,4-dihydroaromatic compounds such as 1,4-dihydrobenzene and 1-benzyl-1,4-dihydronicotinamide and related dienes such as cyclopentadiene and in particular thiols. The thiols were alleged to have greatly increased the yield of the desired dehalogenated product. The thiols could be aliphatic, araliphatic or aromatic and can ". . . carry any substituents such as hydroxy, ether, thioether, keto, carboxyl, esterified carboxyl groups, etc." If further stated that the unsubstituted hydrocarbon groups are preferred. Therefore, while U.S. Pat. No. 3,480,622 disclosed the use of thiols substituted with carboxyl groups, the patent actually taught away from this group by preferring "Unsubstituted hydrocarbon groups," specifying ". . . lower alkyl groups or unsubstituted aryl groups such as phenyl."

It has been discovered that thioglycolic acid surprisingly and unexpectedly increases the yield over that which is expected and greatly simplifies the work-up procedure. The use of thioglycolic acid permits (1) a more versatile choice of reactant medium, (2) faster reactions, (3) greater ease of product isolation and (4) higher yields of 11β-hydroxy steroid product (II or IV).

Virtually all 9α-chloro- or 9α-bromo-11β-hydroxy steroids can be used in the present process. The preferred 9α-halo-11β-hydroxy starting materials (I, III, V, or VII) are well known to those skilled in the art or can be readily prepared by means well known to those skilled in the art from known starting materials. It is preferred that $R_9$ is bromine.

Polar inert solvents such as DMF, THF, and methanol give high yields.

Temperature is not critical, $-50°$ to $100°0$ being suitable, $20°$–$50°$ being preferred.

Upon completion of the reaction as monitored by TLC, the reaction mixture is diluted with a volume of water greater than the total volume of the reaction mixture, preferably 2–10 times the reaction mixture volume. After addition of the water, the reaction mixture is stirred and then filtered. The filter cake is washed and then processed in an appropriate manner, depending on the next chemical reaction it will undergo. The filtrate can be extracted with an organic solvent to obtain additional product.

DEFINITIONS

The definitions and explanations below are for the terms as used throughout the entire patent application, including both the specification and claims.

All temperatures are in degrees Centigrade.
TLC refers to thin-layer chromatography.
GLC refers to gas-liquid chromatography.
THF refers to tetrahydrofuran.
DMF refers to dimethylformamide.
DMSO refers to dimethylsulfoxide.
Saline refers to an aqueous saturated sodium chloride solution.

$R_6$ is a fluorine atom or methyl group.
$R_9$ is a chlorine or bromine atom.
$R_{16}$ is a hydrogen atom or $\alpha$- or $\beta$-methyl or $\alpha$-hydroxyl group, when $R_{16}$ is $\alpha$-hydroxyl and when $R_{17}$ is a hydrogen atom, $R_{16}$ and $R_{17}$ can be a 16,17-acetonide.

$R_{17}$ is a hydrogen atom or a group of the formula —$COR_{17A}$ where $R_{17A}$ is alkyl of 1 thru 4 carbon atoms or phenyl, when $R_{17}$ is a hydrogen atom and when $R_{16}$ is $\alpha$-hydroxyl, $R_{16}$ and $R_{17}$ can be a 16,17-acetonide.

$R_{21}$ is a hydrogen atom or a group of the formula —$COR_{21A}$ where $R_{21A}$ is alkyl of 1 thru 4 carbon atoms or phenyl.

$\sim$ indicates the attached group can be in either the $\alpha$ or $\beta$ configuration.

$\rightleftharpoons$ is a single or double bond.

EXAMPLES

Without further elaboration, it is believed that one skilled in the art can, using the preceding description, practice the present invention to its fullest extent. The following preferred specific embodiments are, therefore, to be construed as merely ilustrative, and not limiting of the preceding disclosure in any way whatsoever.

Example 1 Hydrocortisone acetate (II)

A mixture of 9$\alpha$-bromohydrocortisone acetate (I, 6.90 g) and thioglycolic acid (5.5 ml) in DMF (31 ml) is warmed to 45° with stirring under nitrogen. Over a period of about 5 minutes, a chromous sulfate solution (1.4 M, 13 ml) is added. The resulting mixture is stirred for 10 minutes and then cooled in an ice-water bath. The mixture is diluted with water (200 ml) and stirred at 5° for 30 minutes. The mixture is then filtered and the filter cake washed several times with water. The product is air dried to give the title compound, one spot by TLC, (5.15 g 89.2% chemical yield), which is identical with an authentic sample. An additional 3% of the title compound is obtained by liquid-liquid extraction of the filtrate.

Example 2 6$\alpha$-Fluoro-11$\beta$,16$\alpha$,17$\alpha$,21-tetrahydroxypregn-4-ene-3,20-dione-16,17-acetonide 21-acetate (II)

9$\alpha$-Bromo-6$\alpha$-fluoro-11$\beta$,16$\alpha$,17$\alpha$,21-tetrahydroxypregn-4-ene-3,20-dione-16,17-acetonide 21-acetate (I, 10.8 g) and thioglycolic acid (8.06 ml) are dissolved in DMSO (200 ml) and the mixture under nitrogen is cooled to 15°. Chromous sulfate (0.91 N aqueous solution, 21 ml) is added over a 36-minute period at 15°–16° followed by the addition of water (700 ml, pre-cooled to 1°) over a 2-minute period. The mixture is stirred for 10 minutes and the slurry is then filtered. The solids are washed with water to give the title compound.

Example 3 Prednisolone (II)

Following the general procedure of Example 1 and making non-critical variations but starting with either 9$\alpha$-chloro or 9$\alpha$-bromoprednisolone (I), the title compound is obtained.

Example 4 6$\alpha$-Methylprednisolone (II)

Following the general procedure of Example 1 and making non-critical variations but starting with either 9$\alpha$-chloro or 9$\alpha$-bromo-6$\alpha$-methylprednisolone (I), the title compound is obtained.

Example 5 11$\beta$-Hydroxyandrost-4-ene-3,17-dione (IV)

A solution of 9$\alpha$-bromo-11$\beta$-hydroxyandrost-4-ene-3,17-dione (III, 3.00 g) thioglycolic acid (3.0 ml) in DMF (17 ml) is stirred under nitrogen in a 45°–50° water bath. A chromous sulfate solution (1.4 M, 7.0 ml) is added dropwise over about 5 minutes. The mixture is allowed to cool, and the resulting slurry is diluted by slow addition of water (50 ml). The mixture is cooled to about 5° and filtered. The filter cake is washed with water and air dried to give the title compound (2.03 g, 85.3% chemical yield) which is identical with an authentic sample. The filtrate is extracted to give additional material (0.34 g, 14.3%).

Example 6 11$\beta$-Hydroxyandrost-4-ene-3,17-dione (IV)

A solution of 9$\alpha$-bromo-11$\beta$-hydroxyandrost-4-ene-3,17-dione (III, 2.00 g), thioglycolic acid (2.0 ml) in THF (20 ml) and water (5 ml) is stirred under nitrogen at 20°–25°. A chromous sulfate solution (1.4 M, 5.5 ml) is added and the two-phase system is stirred. After four hours, another 4.5 ml of chromous sulfate solution is added and the mixture stirred overnight. The mixture is diluted with water and extracted with ethyl acetate. The ethyl acetate extracts are washed with water, a diluted sodium hydroxide solution, water and saline. The organic phase is dried over sodium sulfate and concentratd to a solid. The solid is crystallized from benzene-hexane to give a first crop of crystals of the title compound (1.38 g, 83.5% chemical yield) which are measured to be 99% pure as measured by GLC and is identical to an authentic sample.

Example 7 11$\beta$-Hydroxyandrost-4-ene-3,17-dione (IV)

A mixture of 9$\alpha$-bromo-11$\beta$-hydroxyandrost-4-ene-3,17-dione (III, 0.25 g), zinc dust (0.15 g), chromic sulfate hydrate (0.05 g), thioglycolic acid (1 ml) and DMF (20 ml) are stirred under nitrogen at 20°–25° for 20 hours. The crude product is isolated as in Example 3 and is shown by GLC to be the title compound in 83% chemical yield.

Example 8
6α-Fluoro-11β-hydroxy-16α-methylpregna-1,4-diene-3,20-dione (VIII)

Following the general procedure of Example 1 and making non-critical variations but starting with 9α-bromo-6α-fluoro-16α-methylpregna-1,4-diene-3,20-dione (VII) the title compound is obtained.

CHART A

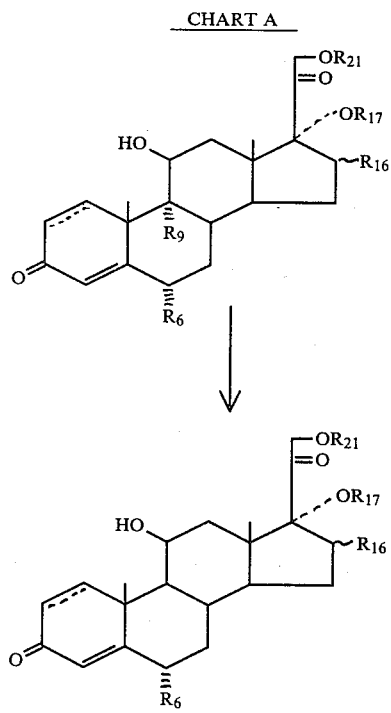

CHART B

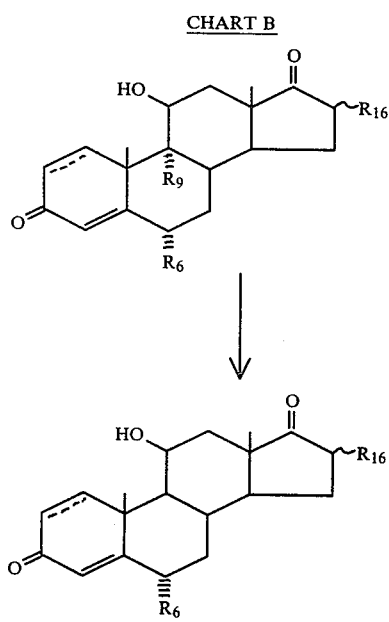

CHART C

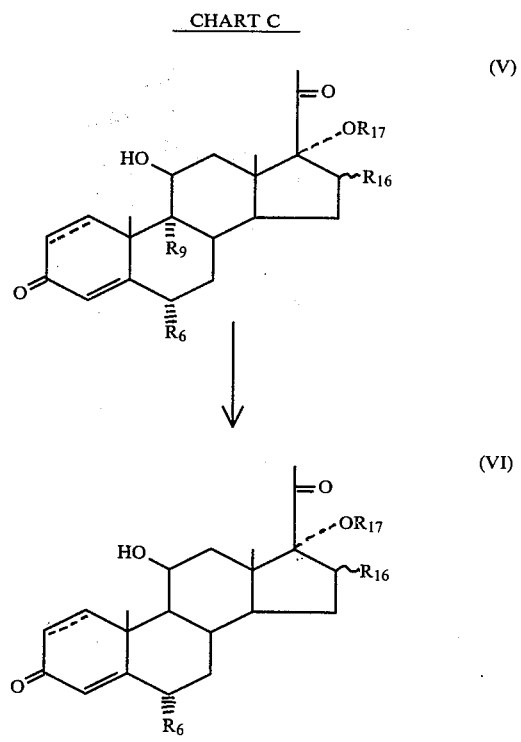

CHART D

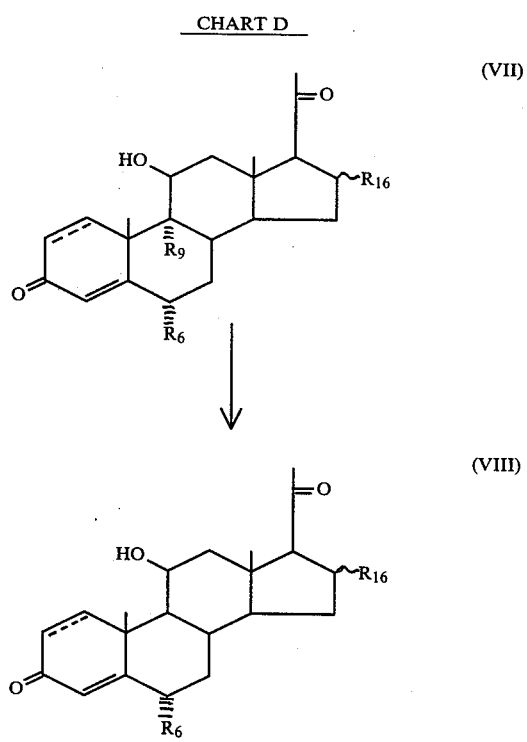

I claim:

1. A process for the preparation of an 11β,17α-dihydroxyprogesterone of the formula

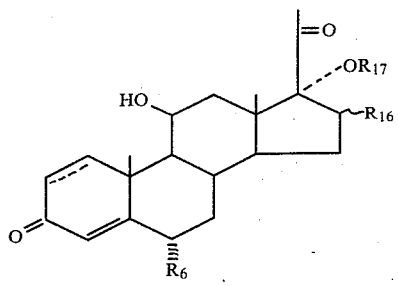

which comprises reacting a 9α-halo-11β,17α-dihydroxyprogesterone of the formula

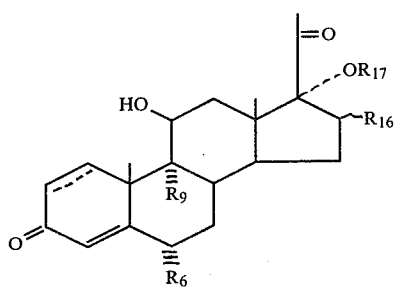

with chromous sulfate or chromous chloride or mixtures thereof and HS—CH$_2$—COOH, where R$_6$, R$_9$, R$_{16}$, R$_{17}$, and ~ are defined in the specification.

2. A process for preparing an 11β-hydroxyprogesterone of the formula

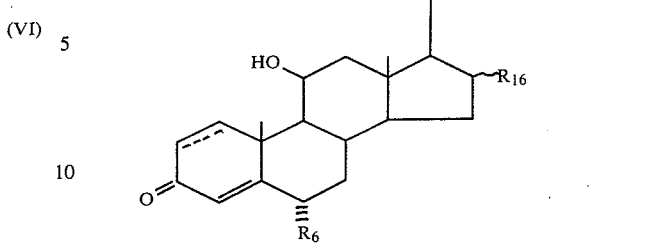

which comprises reacting a 9α-halo-11β-hydroxyprogesterone of the formula

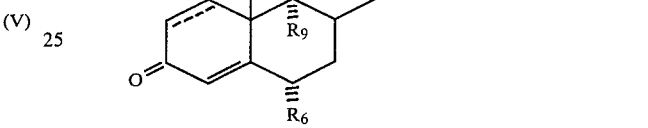

with chromous sulfate or chromous chloride or mixtures thereof and HS—CH$_2$—COOH, where R$_6$, R$_9$, R$_{16}$, R$_{17}$, and ~ are defined in the specification.

3. A process according to claim 1 or 2 which uses chromous sulfate.

4. A process according to claim 1 or 2 which uses chromous chloride.

5. A process according to claim 1 or 2 which uses a mixture of chromous sulfate and chromous chloride.

6. A process according to claim 1 or 2 where R$_9$ is a bromine atom.

7. A process according to claim 1 or 2 where R$_9$ is a chlorine atom.

8. A process according to claim 2 where where the 11β-hydroxyprogesterone (VIII) is 6α-fluoro-11β-hydroxy-16α-methylpregna-1,4-diene-3,20-dione.

* * * * *

UNITED STATES PATENT OFFICE
CERTIFICATE OF CORRECTION

Patent No. 4,325,881     Dated April 20, 1982

Inventor(s) James B. Heather et al

It is certified that error appears in the above-identified patent and that said Letters Patent are hereby corrected as shown below:

Col. 3, line 5: "... to 100°0 being" should read: --... to 100° being--.
Col. 7, line 42: "...$R_{17}$, and ~ are..." should read: --...$R_{17}$, .... and ~ are...--.

Signed and Sealed this

Nineteenth Day of July 1983

[SEAL]

Attest:

GERALD J. MOSSINGHOFF

Attesting Officer     Commissioner of Patents and Trademarks